US010209256B2

(12) United States Patent
Do et al.

(10) Patent No.: US 10,209,256 B2
(45) Date of Patent: Feb. 19, 2019

(54) DEVICES AND METHODS FOR DETECTING NOROVIRUS ON SURFACES

(71) Applicant: KIMBERLY-CLARK WORLDWIDE, INC., Neenah, WI (US)

(72) Inventors: Bao Trong Do, Decatur, GA (US); Jonathan Hofmekler, Sandy Springs, GA (US); Cesar A. Morales, Athens, GA (US); David W. Koenig, Menasha, WI (US); Yang Huang, Shanghai (CN); Aimin He, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/526,939

(22) PCT Filed: Nov. 27, 2014

(86) PCT No.: PCT/CN2014/092404
§ 371 (c)(1),
(2) Date: May 15, 2017

(87) PCT Pub. No.: WO2016/082162
PCT Pub. Date: Jun. 2, 2016

(65) Prior Publication Data
US 2017/0322212 A1  Nov. 9, 2017

(51) Int. Cl.
*G01N 33/547* (2006.01)
*G01N 33/569* (2006.01)
*G01N 33/558* (2006.01)

(52) U.S. Cl.
CPC ..... *G01N 33/56983* (2013.01); *G01N 33/558* (2013.01); *G01N 2333/08* (2013.01); *G01N 2469/10* (2013.01)

(58) Field of Classification Search
CPC ............ A61K 49/0058; Y10S 435/808; Y10S 435/96; Y10S 436/805; A61B 5/0059; A61M 1/16
See application file for complete search history.

(56) References Cited

U.S. PATENT DOCUMENTS 6,153,378 A  11/2000 Liao et al.
6,153,392 A  11/2000 Liao et al.
7,776,542 B1  8/2010 Aoyagi et al.
7,794,928 B2  9/2010 Virgin et al.
2006/0129327 A1  6/2006 Kim et al.
2011/0104300 A1  5/2011 Kim et al.
2012/0258126 A1  10/2012 Schoeller et al.

FOREIGN PATENT DOCUMENTS

| CN | 1675545 A | 9/2005 |
|---|---|---|
| CN | 101187665 A | 5/2008 |
| CN | 101497928 A | 8/2009 |
| CN | 102154528 A | 8/2011 |
| CN | 203759021 U | 8/2014 |
| EP | 0388232 B9 | 1/2005 |
| WO | WO 2007/118209 A2 | 10/2007 |
| WO | WO 2013/083847 A2 | 6/2013 |

OTHER PUBLICATIONS

Catalog of MY BioSource, published on 2006.*
Guo Li et al., "Preparation and Characterization of Monoclonal Antibodies Against Norovirus Capsid Protein," Chinese Journal of Zoonoses, vol. 22, No. 5, ISSN:1002-2694, Dec. 31, 2006, pp. 414-418.
Hsu, C.C. et al., "Development of a Microsphere-Based Serologic Multiplexed Fluorescent Immunoassay and a Reverse Transcriptase PCR Assay to Detect Murine Norovirus 1 Infection in Mice," Clinical and Diagnostic Laboratory Immunology, vol. 12, No. 10, 2005, pp. 1145-1151.
Kellar, K.L., "Applications of Multiplexed Fluorescent Microsphere-Based Assays to Studies of Infectious Disease," Journal of Clinical Ligand Assay, vol. 26, No. 2, 2003, pp. 76-86.
Kunita, Satoshi et al., "Simultaneous Detection of Antibodies to Mouse Hepatitis Virus Recombinant Structural Proteins by a Microsphere-Based Multiplex Fluorescence Immunoassay," Clinical and Vaccine Immunology, vol. 18, No. 5, May 2011, pp. 758-766.

* cited by examiner

*Primary Examiner* — Bao Q Li
(74) *Attorney, Agent, or Firm* — Kimberly-Clark Worldwide, Inc.

(57) ABSTRACT

Lateral-flow assay and time-resolved fluorescence technologies provide a sensitive tool for detecting norovirus particles in a sample. A flow-through assay device employs norovirus and norovirus G2 antibodies. The lateral-flow assay includes a conjugate pad having conjugated probes. The conjugated probes are particles modified with a binding member that is configured to bind with a norovirus. The particles also have a fluorescent label. A general method of detecting the virus includes (i) preparing a sample with contaminants, (ii) processing the sample and depositing it onto the assay device, and (iii) measuring the fluorescence signal.

15 Claims, 1 Drawing Sheet

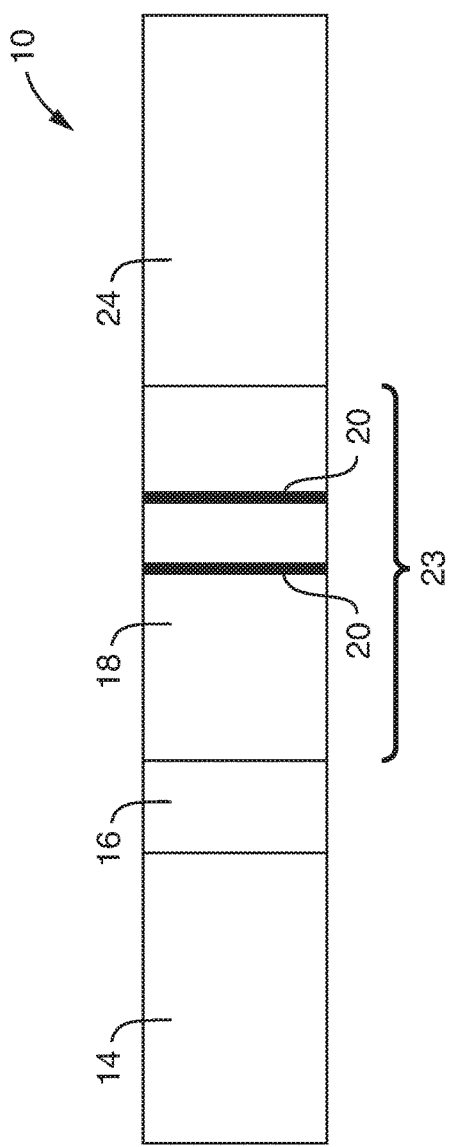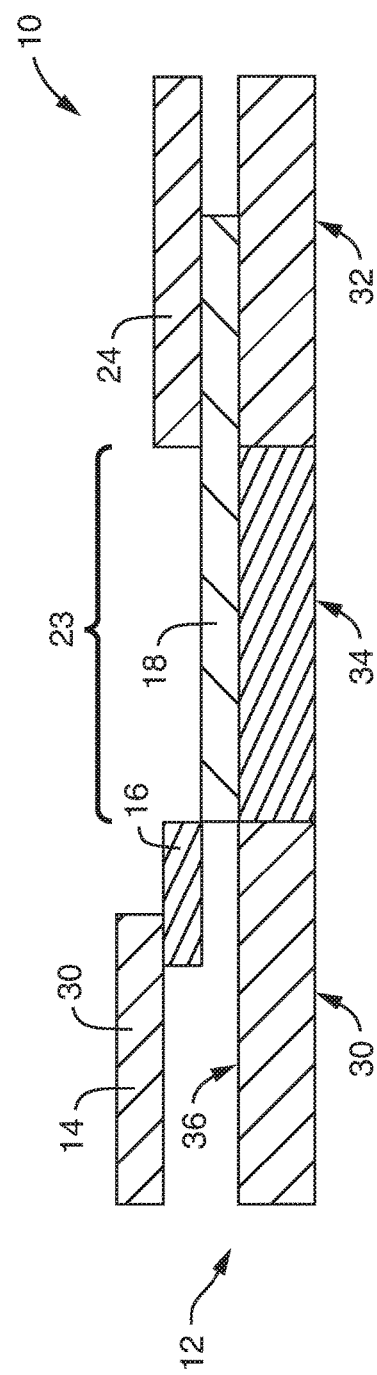

DEVICES AND METHODS FOR DETECTING NOROVIRUS ON SURFACES

TECHNICAL FIELD

The present disclosure relates to devices and methods for the rapid detection of an analyte, in particular, assay devices that employ fluorescent labels to facilitate detection of certain microbes such as norovirus.

BACKGROUND OF THE DISCLOSURE

Norovirus is recognized as the leading cause of nonbacterial acute gastroenteritis. Generally, norovirus genogroups GI and GII are responsible for human gastroenteritis. Studies suggest that genogroup GII, genotype 4 (GII.4) is the primary cause of norovirus infection worldwide.

Noroviruses are highly contagious, so very low doses of viral particles can cause infection. Viral particles are excreted in stool and vomit, and transmission occurs by ingestion of contaminated food or water, and by touching contaminated surfaces. These characteristics can facilitate outbreaks in environments such as schools, day cares, nursing homes, hospitals, and hospitality settings such as ships and hotels. Norovirus infections can be serious, especially for the elderly and young children. Each year in the United States, it is estimated that norovirus causes 570 to 800 deaths.

Rapid detection is important in implementing measures to reduce transmission of the virus. Norovirus detection on hard surfaces is of particular interest. Commercially available assay kits based on immunochromatographic principles (e.g. RT-qPCR assays) have been shown to be inconsistent when used to test hard surfaces, likely because the majority of existing technologies are designed for testing fecal matter or vomitus, where the particle load is high.

As such, a need currently exists for a fast and effective system for detecting low doses of norovirus on surfaces.

SUMMARY OF THE DISCLOSURE

Disclosed is a method and device for detecting the presence of norovirus residing in a test sample. The method includes the following steps:
i) providing a flow-through assay device that comprises a porous membrane in fluid communication with a conjugate pad, the conjugate pad including conjugated probes comprising particles modified with a binding member configured to bind with the norovirus and containing a fluorescent label, the fluorescent label having a fluorescence emission lifetime of greater than about 1 microsecond, the porous membrane defining a detection zone having a test line within which is immobilized a norovirus antibody configured to bind with the norovirus, and a control line positioned downstream from the test line, wherein the control line has immobilized within a norovirus G2 antibody configured to bind with the conjugated probes;
ii) contacting the conjugate pad with the test sample and allowing the particles to flow to the detection zone;
iii) subjecting the test line to pulses of illumination to generate a detection signal and, after a certain period of time has elapsed following a pulse, measuring the intensity of the detection signal, wherein a fluorescence reader is employed to provide the illumination and measure the intensity of the detection signal;
iv) subjecting the control line to pulses of illumination to generate a calibration signal and after a certain period of time has elapsed following a pulse, measuring the intensity of the calibration signal; and
v) comparing the intensity of the detection signal to the intensity of the calibration signal, wherein the amount of the norovirus within the test sample is proportional to the intensity of the detection signal as calibrated by the calibration signal.

The flow-through assay device of the present disclosure includes a porous membrane in fluid communication with a conjugate pad. The conjugate pad has conjugated probes that include particles modified with a binding member configured to bind with the norovirus. The conjugated probes further contain a fluorescent label having a fluorescence emission lifetime of greater than about 1 microsecond. The porous membrane defines a detection zone having a test line within which is immobilized a norovirus antibody configured to bind with the norovirus. The detection zone also has a control line positioned downstream from the test line, wherein the control line includes an immobilized norovirus G2 antibody configured to bind with the conjugated probes.

BRIEF DESCRIPTION OF DRAWINGS

A full and enabling disclosure of the present disclosure, including the best mode thereof, directed to one of ordinary skill in the art, is set forth more particularly in the remainder of the specification, which makes reference to the appended figures in which:

FIG. 1A is a plan view of one embodiment of a membrane-based assay device of the present disclosure; and FIG. 1B is a side view of the membrane-based assay device of FIG. 1A.

Repeat use of reference characters in the present specification and drawings is intended to represent the same or analogous features or elements of the disclosure.

DETAILED DESCRIPTION OF THE DISCLOSURE

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

As used herein, the term "analyte" generally refers to norovirus to be detected. The norovirus used in the methods of the invention can be any type of norovirus, for example, any strain, serotype or isolate of norovirus that infects animals such as humans. The norovirus can be of a genotype generally found in human hosts, such as genotypes GI, GII, and GIV, or any other genotype (e.g., GIII or GV). Particular strains of norovirus that infect human hosts and mammalian hosts include, but are not limited to, Desert Shield virus (Hu/NLV/DSV395/1990/SR) (GenBank Accession number U04469), Lordsdale virus (Hu/NLV/LD/1993/UK) (GenBank Accession number X86557), Mexico virus (Hu/NLV/MX/1989/MX) (GenBank Accession number U22498), Norwalk virus (Hu/NLV/NV/1968/US) (GenBank Accession number M87661), Hawaii virus (Hu/NLV/HV/1971/US) (GenBank Accession number U07611), Snow Mountain virus (Hu/NLV/SMV/1976/US) (GenBank Accession number L23831), Southampton virus (Hu/NLV/SHV/1991/UK) (GenBank Accession number L07418), Alphatron (GenBank Accession number AF195847), murine NoV 1 (GenBank Accession number AY228235), porcine NoV SW918 (GenBank Accession number AB074893), bovine NoV Jena (GenBank Accession number AJ01109), bovine NoV Newbury Agent (GenBank Accession number AF097917), bovine Newbury Agent 1 strain (DQ013304), and bovine Nebraska strain (GenBank Accession number NC_004064).

As used herein, the term "test sample" generally refers to a material suspected of containing the analyte. The test sample can be used directly as obtained from the source or following a pretreatment to modify the character of the sample. The test sample can be pretreated prior to use. Methods of treatment can involve filtration, precipitation, dilution, distillation, concentration, inactivation of interfering components, and the addition of reagents. The test sample can be obtained from hard surfaces. In addition, a solid material suspected of containing the analyte can be used as the test sample. However, it will be necessary to modify a solid test sample to form a liquid medium or to release the analyte.

In general, the present disclosure is directed to a membrane-based assay method and device for detecting the presence of a norovirus residing in a test sample. The device utilizes time-resolved fluorescence to detect the signals generated by excited fluorescent labels (fluorophores). In one possible aspect of the present disclosure, the fluorescent reader used in the present disclosure utilizes a pulsed light-emitting diode (LED) and a silicon photodiode to accurately excite labels and detect fluorescence on a membrane-based assay device without requiring the use of expensive components, such as monochromators or narrow emission band width optical filters. This type of fluorescent reader is shown and described in U.S. Pat. No. 7,632,653, issued to Song et al., and incorporated by reference herein to the extent it is consistent with the present disclosure.

A variety of flow-through assay devices may be constructed according to the present disclosure for use in conjunction with a time-resolved fluorescence detection system. In this regard, various embodiments of the present disclosure will now be described in more detail. It should be understood, however, that the embodiments discussed below are only exemplary, and that other embodiments are also contemplated by the present disclosure. For instance, referring again to FIG. 1A, one system for detecting the presence of an analyte within a test sample is schematically illustrated. Initially, a test sample containing an analyte is applied to the sampling pad 14. From the sampling pad 14, the test sample can then travel to the conjugate pad 16, where the analyte mixes with probes (described below) to form analyte complexes. In one embodiment, for example, the probes are formed from microparticles that are mixed with a lanthanide chelate compound, such as described above, and bound to a specific binding member for the analyte of interest. Moreover, because the conjugate pad 16 is in fluid communication with the porous membrane 18, the complexes can migrate from the conjugate pad 16 to a detection zone 23 present on the porous membrane 18. The detection zone 23 contains an immobilized capture reagent that is generally capable of forming a chemical and physical bond with the probes. For example, binders contain an antibody capable of binding to the specific binding member present on the microparticles.

More specifically, the lateral-flow immunoassay device 10 of the present disclosure is a simple device that can detect relatively low levels of norovirus particles. Referring to FIGS. 1A and 1B, in one aspect of the present disclosure the device 10 may be configured as follows. The device 10 has a bottom end 30 and a top end 32, separated by a midsection 34. A support 12 at the bottom end may be a glass fiber substrate. The midsection 34 of support 12 may be nitrocellulose. The top end of support 12 may be a filter material. Each section may be connected to one another so that a substantially flat surface 36 is created.

Surface 36 supports several capillary components: sample pad 14, conjugate pad 16, membrane 18, and absorption pad 24. In one aspect of the present disclosure, the sample pad 14 does not make direct contact with membrane 18. Instead, the conjugate pad bridges 16 the gap there between. The sample pad 14 lies on top of a portion of conjugate pad 16, overlapping about a 50 percent area of the conjugate pad 16. About a 25 percent area of the conjugate pad 16 is disposed on top of membrane 18.

Membrane 18 overlies the nitrocellulose midsection 34 of support 12, and extends over a portion of the top end 32 made from a filter material. The absorption pad 24 covers the top end 32 completely, overlapping the membrane 18 with about 60 percent of the absorption pad 24 area.

The membrane 18 has two lateral stripes printed thereon, test line 20 and control line 22. The region of the membrane 18 between the conjugate pad and the absorption pad defines the detection zone 23. A third molecule has been immobilized on the test line 20. By the time the sample/conjugate mixture reaches the test line 20, the analyte has been bound on the particle and the third molecule (capture molecule) binds the complex. As more and more fluid passes the test line 20 and control line 22, particles accumulate and the lines 20 and 22 change color. The control line 22 captures any particle and demonstrates that the test has worked. The test line 20 that contains a specific capture molecule only captures those particles onto which the analyte molecule, which may be a norovirus, has been immobilized. After the mixture has passed the control line 22, it reaches the absorption pad 24 as its final destination. The absorption pad 24 merely acts as a waste collector.

In general, a variety of flow-through assay devices may be constructed according to the present disclosure for use in conjunction with a time-resolved fluorescence detection system. In this regard, various embodiments of the present disclosure will now be described in more detail. It should be understood, however, that the embodiments discussed below are only exemplary, and that other embodiments are also contemplated by the present disclosure. Description of the various components of the assay device 10 follows.

Sample Pad:

To initiate the detection of an analyte within the test sample, a user may directly apply the test sample to a portion of the porous membrane 18 through which it can then travel. Alternatively, the test sample may first be applied to a sampling pad 14 that is in fluid communication with the porous membrane 18. Some suitable materials that can be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

Conjugate Pad:

As noted, a test sample travels from the sampling pad 14 to the conjugate pad 16 that is placed in communication with one end of the sampling pad 14. The conjugate pad 16 is formed from a material through which the test sample is capable of passing. For example, in one embodiment, the conjugate pad 16 is formed from glass fibers. Although only one conjugate pad 16 is shown, it should be understood that other conjugate pads may also be used in the present disclosure.

Membrane:

The porous membrane 18 can be made from any of a variety of materials through which the test sample is capable of passing. For example, the materials used to form the porous membrane 18 can include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; nylon membranes; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 18 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

In one embodiment, a suitable nitrocellulose membrane may have a flow rate of about 90 to about 200 seconds/40 mm. In an alternative, the flow rate may be about 110 to about 165 seconds/40 mm, about 140 to about 200 seconds/40 mm, or more suitably, 90 to 150 seconds/40 mm. The pore size may range from about 5 to about 10 micrometers, or 7 to 9 micrometers or more suitably, about 8 micrometers. The thickness of the may range from about 125 to about 200 micrometers, about 155 to 200 micrometers, or more suitably about 200 micrometers. For instance, one suitable nitrocellulose membrane may be obtained from Starious, Germany, sold as UNISTART 95: it has a flow rate of 135 seconds/40 mm, a pore size of 200 micrometers, and a thickness of 150 micrometers.

Absorption (Wicking) Pad:

The absorption pad 24 generally receives fluid that has migrated through the entire porous membrane 18. As is well known in the art, the absorption pad 24 can assist in promoting capillary action and fluid flow through the membrane 18.

Support:

The support 12, described supra, is rigid enough to prevent bending during the intended use of the device 10 as described herein. One suitable support 12 is MILLIPORE HF000MC100; Lot NO. 065170-01, available from EMD Millipore, Billerica, Mass.

Sample:

In one aspect of the disclosure a running buffer is made from the following formula: 10 mM HEPES buffer+3% S9 surfactant+1% bovine serum albumin "BSA". The S9 surfactant is TRITON X 100 available from Sigma-Aldrich, St. Louis, Mo., USA. The HEPES buffer is 2-[4-(2-Hydroxyethyl)-1-piperazinyl]ethanesulfonic acid. In one aspect of the disclosure, the norovirus in the sample is present in the running buffer at about $10^5$ to $10^9$ particles per sample, or at least about $2.5 \times 10^5$ virus particles per sample. The norovirus-positive sample can be any suitable volume, for example, 100 microliter. Any range of sample volume between about 90-110 microliter can be used.

Conjugate (Labels):

To facilitate accurate detection of the presence or absence of an analyte within the test sample, labels are applied at various locations of the device 20. The labels may be used for both detection of the analyte and for calibration. At least a portion of the labels used in device 20 contain a fluorescent compound. In general, such fluorescent compounds can be fluorescent molecules, polymers, dendrimers, particles, and the like.

In accordance with the present disclosure, the fluorescent labels are configured to allow "time-resolved fluorescence detection." Time-resolved fluorescence involves exciting the fluorescent label with a short pulse of light, then typically waiting a certain time (e.g., between approximately 100 to 200 microseconds) after excitation before measuring the remaining long-lived fluorescent signal. In this manner, any short-lived fluorescent background signals and scattered excitation radiation are eliminated. Time-resolved fluorescence detection is designed to reduce background signals from the emission source or from scattering processes (resulting from scattering of the excitation radiation) by taking advantage of the fluorescence characteristics of certain fluorescent materials.

The selection criteria of particularly desired labels for time-resolved fluorescence include a relatively long emission lifetime. This is desired so that the label emits its signal well after any short-lived background signals dissipate. Furthermore, a long fluorescence lifetime makes it possible to use low-cost circuitry for time-gated fluorescence measurements. For example, fluorescent labels used in the present disclosure may have a fluorescence lifetime of greater than about 1 microsecond, in some embodiments greater than about 10 microseconds, in some embodiments greater than about 50 microseconds, and in some embodiments, from about 100 microseconds to about 1000 microseconds. In addition, the fluorescent label may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of the fluorescent label to remain far apart from its emission wavelengths and is desirable because a large difference between excitation and emission wavelengths makes it easier to eliminate the reflected excitation radiation from the emitted signal. Further, a large Stokes shift also minimizes interference from fluorescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the fluorescent labels have a Stokes shift of greater than about 50 nanometers, in some embodiments greater than about 100 nanometers, and in some embodiments, from about 250 to about 350 nanometers.

The fluorescent labels may be used in a variety of ways to form a probe. For example, the fluorescent labels may be used alone to form probes. Alternatively, the fluorescent labels may be used in conjunction with polymers, liposomes, dendrimers, and other micro- or nano-scale structures to form probes. In addition, the labels may be used in conjunction with microparticles (sometimes referred to as "beads" or "microbeads") to form probes. For instance, naturally occurring microparticles, such as nuclei, mycoplasma, plasmids, plastids, mammalian cells (e.g., erythrocyte ghosts), unicellular microorganisms (e.g., bacteria), polysaccharides (e.g., agarose), silica, glass, cellulose-based particles, and the like, can be used. Further, synthetic microparticles may also be utilized. For example, in one embodiment, latex microparticles that are labeled with a fluorescent or colored dye are utilized. Although any latex microparticle may be used in the present disclosure, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and the like, or an aldehyde, carboxyl, amino, hydroxyl, or hydrazide derivative thereof. Other suitable microparticles may be described in U.S. Pat. No. 5,670,381 to Jou, et al. and U.S. Pat. No. 5,252,459 to Tarcha, et al., which are incorporated herein in their entirety by reference thereto to the extent they are consistent herewith.

The probes are modified so they are more readily able to bond to the analyte. In such instances, the probes are modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members can include a monoclonal or polyclonal antibody, a recombinant protein or a mixture(s) or fragment(s) thereof, as well as a mixture of an antibody and other specific binding members. In one aspect of the disclosure, the binding member is antibody 1513F, Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

The coupling of the antibody with fluorescent microspheres may be performed as follows. An indirect immunofluorescence method is used. Immunofluorescence (IF) or (IFA) is a common laboratory technique. It is a form of light microscopy used mainly on microbiological samples utilizing the specificity of an antibody for its target protein or epitope to bind a molecule of fluorescent dye to a specific target within a solution. Following successful Immunofluorescence of a sample, it becomes possible to visualize the target molecule using a fluorescence microscope or automated reader. The primary antibody specific for the molecule of norovirus is unlabeled, and a second anti-immunoglobulin antibody directed the secondary antibody is tagged with the fluorescent dye.

In one aspect of the disclosure, norovirus antibodies were coupled with the fluorescent microspheres (d=110 nm, Lumigenex, Suzhou, China). Fluorescent microspheres were washed with 80% ethanol once, and a 20 mM MES washing buffer (2-(N-morpholino)ethanesulfonic acid) three times. Washed microspheres were activated by 1-Ethyl-3-(3-dimethylaminopropyl)carbodiimide ("EDC") at ambient temperature for 15 min, and washed again three times with the same washing buffer. (EDC is a heterobifunctional, water-soluble, zero-length carbodiimide crosslinker that is used to couple carboxyl groups to primary amines.) The fluorescent micropheres were coupled with norovirus anti-body from Fitzgerald Industry International, MA, USA 10-1513 and left to incubate at a temperature of 4° C., overnight. The uncoupled sites are blocked with a blocking buffer (10 mM PBS with 5% BSA). After washing three times with the washing buffer, the conjugated microspheres were resuspended in a storage buffer (10 mM PBS, pH 7.4) to a final concentration of 1% solids, and stored at 4° C.

Test and Control Lines:

For the detection of a virus such as norovirus, the test line antibody may be a norovirus antibody such as monoclonal antibody 4901-RAb2, available from Virostat, Inc., Portland, Me. ("VIROSTAT"). Other suitable antibodies may be obtained for other viruses, as desired.

For the detection of a virus such as norovirus, the control line antibody may be a norovirus G2 antibody such as monoclonal antibody 10-1513 available from Fitzgerald Industries International, Acton, Mass. ("Fitzgerald"). Other suitable antibodies may be obtained for other viruses, as desired.

The test line 20 and control line 22 are spaced apart a distance of about 4 to about 15 mm, or in the alternative, about 5 to about 10 mm, or in the alternative, about 6 mm.

Although various embodiments of device configurations have been described above, it should be understood, that a device of the present disclosure may generally have any configuration desired, and need not contain all of the components described above.

Method

Generally, the method of the present disclosure uses lateral-flow assay and time-resolved fluorescence technologies to provide a sensitive tool for detecting norovirus particles in a sample. The method of use combines (i) preparing a sample with contaminants, (ii) processing the sample and depositing it onto the assay strip as described surpra, and (iii) measuring the fluorescence signal.

In one aspect, sampling is done by wiping a surface suspected of harboring a viral contaminant (analyte) with a swab (not shown). The surface area sampled may be about 25 $cm^2$. The material of the swab is such that it can lift an adequate amount of viral samples from the surface, and subsequently release the viral sample onto the sampling pad 14. Any type of swab may be used as long as the material of the swab does not cross react with the analyte. One example of a swab may be a cotton-tipped plastic stick. The swab is inserted into a sample collection tube and swirled in the assay diluent at least 10 times. The swab may be processed by vortexing in a PBS pH 7.4 buffer to release the analyte.

The test sample containing the analyte is applied to the sampling pad 14. From the sampling pad 14, the test sample travels to the conjugate pad 16, where the analyte mixes with probes (described supra) to form analyte complexes. Because the conjugate pad 16 is in fluid communication with the porous membrane 18, the analyte complexes then migrate from the conjugate pad 16 to a detection zone 23 present on the porous membrane 18. The detection zone 23 contains an immobilized capture reagent/antibody at test line 20 that is generally capable of forming a chemical or physical bond with the probes. The capture reagent/antibody are capable of binding the present antibody of choice onto the microparticles, which is in one embodiment, a norovirus antibody. The secondary antibody binds the primary antibody which is conjugated on the microparticles surface via a covenant bond.

In one embodiment, a time-resolved fluorescence immunoassay method for detecting the presence or quantity of an analyte in a test sample includes the following steps:

i) placing a time-resolved fluorescence reader (not shown) proximate to the detection zone 23, the fluorescence reader comprising a pulsed excitation source and a time-gated detector;

ii) exciting the fluorescent label at the detection zone 23 with the pulsed excitation source, wherein the excitation causes the fluorescent label to emit a detection signal; and iii) measuring the intensity of the detection signal with the time-gated detector.

Once captured, the fluorescence signal of the probes at the detection zones can be measured using a time-resolved fluorescence reader. The fluorescence reader may be constructed to successively emit pulsed light onto the detection zone as disclosed in U.S. Pat. No. 7,632,653, incorporated herein by reference to the extent it is consistent herewith.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A method for detecting a presence of norovirus residing in a test sample, said method comprising:

i) providing a flow-through assay device that comprises a porous membrane in fluid communication with a conjugate pad, the conjugate pad comprising conjugated probes having particles modified with a binding member configured to bind with the norovirus and containing a fluorescent label, wherein the fluorescent label has a fluorescence emission lifetime of greater than about 1 microsecond; and wherein the porous membrane defines a detection zone comprising a test line within which is immobilized a norovirus antibody configured to bind with the norovirus, and a control line positioned downstream from the test line, wherein the control line has immobilized within a norovirus G2 antibody configured to bind with the conjugated probes;

ii) contacting the conjugate pad with the test sample and allowing the particles to flow to the detection zone;

iii) subjecting the test line to pulses of illumination to generate a detection signal and, after a certain period of time has elapsed following a pulse, measuring an intensity of the detection signal, wherein a fluorescence reader is employed to provide an illumination and measure the intensity of the detection signal, iv) subjecting the control line to pulses of illumination to generate a calibration signal and after a certain period of time has elapsed following a pulse, measuring an intensity of the calibration signal; and v) comparing the intensity of the detection signal to the intensity of the calibration signal, wherein the amount of the norovirus within the test sample is proportional to the intensity of the detection signal as calibrated by the calibration signal.

2. The method of claim 1 wherein the test sample comprises at least $10^5$ to $10^9$ norovirus particles in a running buffer.

3. The method of claim 1 wherein the test sample comprises at least $2.5 \times 10^5$ norovirus particles in a running buffer.

4. The method of claim 2 wherein the running buffer comprises:
   10 mM 2-[4-(2-Hydroxyethyl)-1-piperazinyl]ethanesulfonic acid;
   3% by weight S9 surfactant; and
   1% by weight bovine serum albumin.

5. The method of claim 1, wherein the binding member is selected from the group consisting of biotin and avidin; biotin and streptavidin; antibody-binding protein A and antibodies, carbohydrates and lectins; antibody-binding protein G and antibodies, carbohydrates and lectins; complementary nucleotide sequences; and complementary peptide sequences.

6. The method of claim 1, wherein the binding member comprises a monoclonal antibody.

7. The method of claim 5 wherein the binding member is an analog having at least one epitope in common with the norovirus.

8. The method of claim 1, wherein the fluorescent label comprises a lanthanide chelate of samarium, dysprosium, europium, terbium, or combinations thereof.

9. The method of claim 1, wherein the fluorescent label is europium chelate.

10. A flow-through assay device for detecting norovirus in a sample, the device comprising:

a porous membrane in fluid communication with a conjugate pad, the conjugate pad comprising conjugated probes having particles modified with a binding member configured to bind with the norovirus and containing a fluorescent label, wherein the fluorescent label has a fluorescence emission lifetime of greater than about 1 microsecond; and wherein the porous membrane defines a detection zone having a test line within which is immobilized a norovirus antibody configured to bind with the norovirus, and a control line positioned downstream from the test line, wherein the control line has immobilized within a norovirus G2 antibody configured to bind with the conjugated probes.

11. The flow-through assay device of claim 10, wherein the binding member comprises a monoclonal antibody.

12. The flow-through assay device of claim 10 wherein the particles are mixed with a lanthanide chelate compound.

13. The flow-through assay device of claim 10 wherein the porous membrane is a nitrocellulose membrane having a flow rate or 90 to 200 seconds per 40 mm test sample.

14. The flow-through assay device of claim 10 wherein the porous membrane is a nitrocellulose membrane having a pore size ranging from 5 to 10 micrometers.

15. The flow-through assay device of claim 10 wherein the porous membrane is a nitrocellulose membrane having a thickness of 125 to 200 micrometers.

* * * * *